United States Patent [19]

Kolp

[11] Patent Number: 5,663,457
[45] Date of Patent: Sep. 2, 1997

[54] METHODS FOR PREPARING ALKYLATED HYDROXYAROMATICS

[75] Inventor: Christopher Jay Kolp, Euclid, Ohio

[73] Assignee: The Lubrizol Corporation, Wickliffe, Ohio

[21] Appl. No.: 603,949

[22] Filed: Feb. 16, 1996

[51] Int. Cl.$^6$ .................................................. C07C 37/14
[52] U.S. Cl. ........................... 568/790; 568/792; 568/766
[58] Field of Search ................................ 568/790, 766

[56] References Cited

U.S. PATENT DOCUMENTS

| | | | |
|---|---|---|---|
| 3,037,052 | 5/1962 | Bortnick | 260/485 |
| 4,152,499 | 5/1979 | Boerzel et al. | 526/52.4 |
| 4,238,628 | 12/1980 | Cahill et al. | 568/736 |
| 4,323,714 | 4/1982 | Malloy et al. | 568/766 |
| 4,605,808 | 8/1986 | Samson | 585/525 |
| 4,849,569 | 7/1989 | Smith | 585/446 |
| 5,019,669 | 5/1991 | Adams et al. | 585/446 |
| 5,080,871 | 1/1992 | Adams et al. | 422/187 |
| 5,300,701 | 4/1994 | Cherpeck et al. | 568/792 |

FOREIGN PATENT DOCUMENTS

| | | | |
|---|---|---|---|
| 0355895 | 12/1994 | European Pat. Off. | C08F 8/46 |
| 1159368 | 7/1969 | United Kingdom | C08F 27/00 |

*Primary Examiner*—Bernard Dentz
*Assistant Examiner*—Sreeni Padmanabhan
*Attorney, Agent, or Firm*—William J. Connors; Frederick D. Hunter

[57] ABSTRACT

Conventional low vinylidene polyolefins are condensed with hydroxyaromatics under the influence of macroreticular ion exchange resins in acid form to yield alkylated hydroxyaromatics.

6 Claims, No Drawings

METHODS FOR PREPARING ALKYLATED HYDROXYAROMATICS

BACKGROUND OF THE INVENTION

It is known in the art that hydroxyaromatics may be alkylated with polybutenes and other polyolefins derived from $C_2$–$C_6$ olefins to form alkylated hydroxyaromatic compounds. The alkylated hydroxy aromatic compounds such as alkylated phenol are important lubricant and fuel additives. U.S. Pat. No. 5,300,701 to Cherpeck describes the alkylation of hydroxyaromatics with polyisobutylene (PIB) in the presence of acidic alkylation catalyst to give polybutenyl hydroxyaromatic compounds. The polyisobutylene (PIB) used in the '701 patent has a methylvinylidene content of at least about 70%. The PIB used by Cherpeck had a number average molecular weight of 300–5,000.

The acidic alkylation catalysts employed by Cherpeck were Lewis acids, trifluoromethane sulfonic acid, and acidic molecular sieves. Typical acid catalysts are aluminum chloride, boron trifluoride etherate, trifluoromethane sulfonic acid and Amberlyst® molecular sieve-type catalyst. The Cherpeck 5,300,701 patent is included herein by reference in its entirety.

A concern in running PIB alkylation reactions is fragmentation of the alkylating agent and alkyl substituent. In the Cherpeck patent, this is minimized by using a high vinylidene PIB having greater than 70% methyl vinylidene terminal units in the PIB. Other solutions to minimizing fragmentation are disclosed in British Patent 1,159,368 which used boron trifluoride-phenolate at 0°–65° C. as the acidic alkylating catalyst.

Cahill in U.S. Pat. No. 4,238,628 reduces fragmentation of the alkylating agent by using boron trifluoride with a $C_3$ or higher olefin polymer having a terminal ethylene unit. In the preferred mode of Cahill, polybutene is first reacted with ethylene to provide a polymer having terminal ethylene units for ease of alkylation reaction with benzene, phenol and napthol. The yields on alkylation with the ethylene-terminated polymers range from 44–64%. The Cahill U.S. Pat. No. 4,238,628 is incorporated herein by reference in its entirety.

Alkylation reactions of hydroxyaromatics with polyolefins as pointed out above rely on using a highly reactive alkylating agent having terminal unsaturation so that mild reaction conditions may be employed. The highly reactive alkylating species also provide for high yields of alkylated hydroxy aromatics. The reaction species in the Cherpeck '701 patent cited above is a terminal methyl vinylidene unit in the alkylating agent. The methyl vinylidene unit is represented by $R(CH_3)C=CH_2$ wherein R is hydrocarbyl or polymeric.

The reactive species in the Cahill '628 patent cited above is a terminal ethylene or vinyl unit $RCH=CH_2$ which is formed by condensing a polymer such as polybutene with ethylene. R is also hydrocarbyl or polymeric.

High vinylidene PIBs as described in the '701 patent are disclosed and claimed in U.S. Pat. Nos. 4,152,499 to BASF and 4,605,808 to BP. The high vinylidene PIBs of the respective companies are sold under the trade names of Glissopal® and Ultravis®. The '499 and '808 patents are incorporated herein by reference for their disclosure of the synthesis of high vinylidene PIBs.

European Patent Specification Publication 0355 895 details the structure of isomers near the terminus of PIBs and explains reactivity of the PIBs on the basis of isomer content. EPO 0355 895 is herein incorporated by reference for material pertinent to this disclosure.

The '701 patent recites Amberlyst® 36 as a suitable catalyst for use in alkylating hydroxyaromatics with high vinylidene PIB but discloses no experimental data. Bortnick, in U.S. Pat. No. 3,037,052 discloses the use of a macroreticular structured sulfonic cation exchanger to catalyze alkylation of phenol with $C_4$–$C_9$ terminal olefins. Malloy in U.S. Pat. No. 4,323,714 describes alkylating hydroxyaromatics with $C_2$–$C_{10}$ terminal olefins with fluoro-sulfonic acid resins available from DuPont under the trademarked name Nafion®. Similarly, U.S. Pat. No. 4,849,569 discloses alkylating aromatics including hydroxyaromatics with $C_2$–$C_{20}$ olefins with zeolite-type catalysts and sulfonated ion exchange catalysts such as Amberlyst® 15. There is no disclosure of experimental detail in the '569 patent of Amberlyst® 15, hydroxyaromatic, olefin reaction product. U.S. Pat. Nos. 5,019,669 and 5,080,871 also describe using $C_2$–$C_{20}$ olefins to alkylate aromatics including hydroxyaromatics using zeolites and sulfonated ion exchange resins. The olefins used have terminal unsaturation.

SUMMARY OF THE INVENTION

As described above, it is known to synthesize high vinylidene PIBs and that such PIBs are reactive and may be used under mild conditions to alkylate hydroxyaromatics to form polybutenyl hydroxyaromatics.

We have discovered that by proper selection of catalyst, conventional PIBs synthesized in the customary way using $AlCl_3$ catalyst may be used to alkylate hydroxyaromatics under milder, and more environmental-friendly conditions using a simpler process. The discovery is that conventional PIBs under the influence of cationic resins in acid forms may be used to alkylate hydroxyaromatics in high yield.

In the synthesis of alkylated hydroxyaromatics such as polybutenyl phenol by conventional processes, PIB and phenol are reacted under the influence of strong Lewis acids such as $BF_3$/phenol to produce the polybutenyl phenols. In conventional processes, problems can arise from separation of the catalyst from reactants and in disposal of the waste stream generated in the reaction. However, conventional PIBs are less expensive than high vinylidene PIBs so there is an economic incentive to use them.

DETAILED DESCRIPTION OF THE INVENTION

In this invention, a conventional PIB is condensed under influence of a cation exchange resin in acid form with a hydroxyaromatic to produce a polybutenyl hydroxyaromatic in high yield. Polybutenyl phenol is an example of a product produced by this method. Conventional PIB is produced by acid catalyzed polymerization of a $C_4$- raffinate of a cat cracker or ethylene plant butane/butene stream.

Conventional PIB has terminal vinylidene content of roughly 5%. The terminal isomer groups of conventional PIB and high vinylidene PIB are given below in Table 1 and are those published in EPO 0355 895. However, in this invention intermediate vinylidene content PIBs may also be used. Such intermediate PIBs have a vinylidene content of less than 45% and can range down to the 4–5% vinylidene content of conventional PIBs.

TABLE 1

| PIB Terminal Groups | Percent in Conventional PIB | Percent in High Vinylidene PIB |
|---|---|---|
| $-\underset{\underset{CH_3}{|}}{\overset{\overset{CH_3}{|}}{C}}-CH_2-\underset{}{\overset{\overset{CH_3}{|}}{C}}=CH_2$  I | 4–5% | 50–90% |
| $-\underset{\underset{CH_3}{|}}{\overset{\overset{CH_3}{|}}{C}}-CH-C\underset{CH_3}{\overset{CH_3}{\diagup\!\!\diagdown}}$  II | | 6–35% |
| $-CH_2-\underset{\underset{CH_3}{|}}{C}=CH-CH_3$  III | 63–67% | absent or minor |
| $-\overset{\overset{CH_3}{|}}{CH}-\overset{\overset{CH_3}{|}}{C}=C\underset{CH_3}{\overset{CH_3}{\diagup\!\!\diagdown}}$  IV | 22–28% | 1–15% |
| $-\overset{\overset{CH_3}{|}}{C}=\overset{\overset{CH_3}{|}}{C}-CH\underset{CH_3}{\overset{CH_3}{\diagup\!\!\diagdown}}$  IVA | | |
| $-CH_2-\overset{\overset{CH_2}{\|\|}}{C}-CH_2-$  V | 5–8% | 0–5% |
| Other | 0–10% | 0–10% |

As can be seen from the above structures, conventional PIB is characterized by very low terminal vinylidene groups (I) and isomers in acid catalyzed equilibrium therewith (II). Conventional PIB further comprises a distinct tri-substituted terminal olefin group (III) which is nearly absent or present in only a low level in high vinylidene PIB. The distinct terminal group III is a 2-butene in which the 2-carbon is tri-substituted.

Structure IVA above is an acid-catalyzed rearrangement product of IV while V is an internal vinylidene group. The terminal group content of conventional and high vinylidene PIBs have been determined by NMR analysis. Conventional PIBs are commercially available under various tradenames including Parapol® from Exxon, Lubrizol® 3104, 3108 and Indopol® from Amoco and Hyvis® from BP. Conventional PIBs have number average molecular weight in the range of 300–5000, but the preferred number average molecular weight is in the range of 500–2000. In the context of this invention, PIB stands as a representative of all $C_2$–$C_6$ polyolefins with roughly the same terminal group composition.

The catalysts of choice for the conventional PIB alkylation of phenol are macroreticular resins. The choice macroreticular resins are sulfonated polystyrenes in their acid form. While many such catalysts are available under the above definition, care was taken to discover which catalysts would accomplish the alkylation reaction in sufficient yield over a satisfactory time period. The standard parameters chosen for selecting a satisfactory catalyst were at least a 50% conversion of conventional PIB to the alkylated polybutenyl phenol compound in 24 hours or less and at a temperature of 70° C. or less, and a PIB/phenol mole ratio of 1:3 and using 7 weight percent catalyst and a conventional PIB of about 1000 number average molecular weight.

Ion exchange resin catalysts in the acid form which were found to catalyze the alkylation of phenol with conventional PIB according to standard parameters stated above were Amberlyst® 35 and 18 and Purolite® CT-165. Forcing conditions could be used in the alkylation reaction to produce polybutenyl phenol. Such conditions would include temperatures up to 90° C. for the reaction. Also, increased amounts of phenol and catalyst could be used. Longer reaction times could also be used. In practice, the preferred PIB/phenol mole ratio is about 1:5 and the preferred amount of catatyst is about 12% weight percent.

The parameters controlling which macroreticular ion exchange resin in acid form will satisfy the above results for alkylating phenol with PIB are unclear. However, one can speculate that both the exchange capacity and the average pore size of the resin come into play. The average pore size in angstroms and exchange capacity in milliequivalents/grams for several Amberlyst® resins is given below in Table 2.

TABLE 2

| Macroreticular Resin Catalyst | Average Pore Diameter Å | Capacity meq/g (dry) |
|---|---|---|
| (1) Amberlyst ®35 (wet) | 250 | 5.2 |
| (2) Amberlyst ®18 (wet) | 450 | 4.7 |
| (3) Amberlyst ®36 (wet) | 165 | 5.4 |
| (4) Amberlyst ®15 (dry) | 245 | 4.8 |

Catalyst (1) with medium average pore diameter and high capacity satisfies the standard reaction parameters outlined above while catalyst (4) with equivalent average pore diameter but lesser capacity will not. Catalyst (2) with high average pore diameter and low capacity will satisfy standard reactivity criteria stated above while catalyst (3) which has low average pore size but high capacity will not satisfy standard reactivity criteria stated above. The precise balance of average pore size and capacity has not been determined.

The conventional PIBs are commercially available in several number average molecular weight ranges. Alternatively, a conventional PIB may be synthesized from isobutylene and $AlCl_3$. In this synthesis, 2.6 moles isobutylene was added to 0.0295 moles of aluminum chloride being stirred in hexane under nitrogen in a –40° C. bath. Isobutylene was cooled to –78° C. with dry ice/isopropanol and added dropwise to the $AlCl_3$. Following addition which is exothermic, the reaction mixture was poured into a beaker containing a 7% sodium hydroxide solution. The organic layer was separated, washed with aqueous sodium chloride solution and stripped on an evaporator at 100° C. under reduced pressure.

Relative amounts of end units in conventional PIBs and high vinylidene PIBs were determined from NMR spectra made using a Burker AMX 500 or 250 instrument and UXNMRP software to workup the spectra. The spectra were determined in $CDCl_3$ at 300 or 500 MHz.

A standard synthesis of a conventional polybutenyl phenol product is made by reacting dried phenol and dried Amberlyst catalyst mixed with cyclohexane at 70° C. under $N_2$ with a conventional PIB having number average molecular weight of about 1000. The reaction was run for 24 hours and the resin separated by filtration. The reaction mixture was vacuum stripped at 220° C. and 20 mm Hg to remove volatiles. The yield of product was about 70% based on the weight of starting conventional PIB. The temperature for the alkylation reaction is not allowed to go above 70° C. so that the formation of t-butylphenol is minimized. Anhydrous conditions promote reactivity of the catalyst because water has been shown to tie up sulfonate groups in the catalyst and thus reduce its acidity.

What is claimed is:

1. A method of preparing a polybutenyl substituted hydroxyaromatic compound, said method comprising:
   A. forming a mixture of cyclohexane and a conventional polyisobutylene (PIB), a hydroxyaromatic compound and a macroreticular resin catalyst in acid form;
   B. reacting said mixture at temperatures up to about 70° C. and for times up to about 24 hours wherein by said reacting at least about a 50% yield of said polybutenyl substituted hydroxyaromatic compound results; and
   wherein said resin is selected for meeting said yield parameters within said time and temperature parameters.

2. A method according to claim 1, wherein said PIB has $\overline{Mn}$ 300–5,000.

3. A method according to claim 1, wherein said resin catalyst in acid form is selected from Amberlyst 35, Amberlyst 18 or Purolite CT-resins or mixtures thereof.

4. A method according to claim 1, wherein the ratio of said PIB to said hydroxyaromatic compound is 1:6 to 1:1.

5. A method for making polybutenyl substituted phenol, said method comprising:
   A. forming a mixture of cyclohexane, phenol, polyisobutylene (PIB) having $\overline{Mn}$ in the range of 500–2,500, and Amberlyst 35 catalyst in acid form comprising 6–12 weight percent of said mixture, and the ratio of PIB to phenol being 1:2 to 1:6; and
   B. reacting said mixture at time/temperature parameters not to exceed about 24 hours and 70° C. to give a yield of at least about 50% polybutenyl phenol.

6. The product formed from the methods of claims 2 and 5.

\* \* \* \* \*